US009910003B1

(12) United States Patent
Lastinger et al.

(10) Patent No.: US 9,910,003 B1
(45) Date of Patent: Mar. 6, 2018

(54) METHODS AND APPARATUS FOR A MOISTURE DETECTOR

(71) Applicant: Helvetia Wireless LLC, Scottsdale, AZ (US)

(72) Inventors: Roc Lastinger, Cave Creek, AZ (US); Brian C. Woodbury, Gilbert, AZ (US)

(73) Assignee: Helvetia Wireless, LLC, Scottsdale, AZ (US)

( * ) Notice: Subject to any disclaimer, the term of this patent is extended or adjusted under 35 U.S.C. 154(b) by 209 days.

(21) Appl. No.: 14/885,220

(22) Filed: Oct. 16, 2015

Related U.S. Application Data

(60) Provisional application No. 62/093,805, filed on Dec. 18, 2014.

(51) Int. Cl.
*G01N 27/04* (2006.01)
*G01N 27/06* (2006.01)
*G01R 27/02* (2006.01)
*G01N 27/12* (2006.01)

(52) U.S. Cl.
CPC .................................. *G01N 27/121* (2013.01)

(58) Field of Classification Search
CPC .... G01N 27/048; G01N 27/06; G01N 27/121; G01R 27/02
See application file for complete search history.

(56) References Cited

U.S. PATENT DOCUMENTS 2,737,615 A 3/1956 Roby
3,145,567 A 8/1964 Bobrowsky
4,319,232 A 3/1982 Westphal
4,350,968 A 9/1982 Tokarz
4,386,231 A 5/1983 Vokey
4,411,155 A 10/1983 Coulange
4,594,638 A 6/1986 Suzuki
4,677,371 A 6/1987 Imaizumi
4,928,513 A 5/1990 Sugihara
5,220,514 A 6/1993 John
(Continued)

FOREIGN PATENT DOCUMENTS

CA 2312368 4/2000
EP 558057 9/1993
(Continued)

*Primary Examiner* — Jermele M Hollington
*Assistant Examiner* — Neel Shah
(74) *Attorney, Agent, or Firm* — Letham Law Firm LLC; Lawrence Latham

(57) ABSTRACT

A system for detecting the presence of a liquid. The system includes a sensor, a cap, and a reader. The sensor includes at least three conductors, a substrate, and a cover. The conductors are positioned between the substrate and the cover. The cover includes a first portion at a first position and a second portion at a second position. The first portion and the second portion are adapted for separation from proximate portions of the cover and from the substrate to expose the conductors. The cap and the reader are adapted for positioning against the substrate at the first position and the second position respectively after separation of the first portion or the second portion. Positioning the cap against the against the substrate electrically couples two of the at least three conductors to each other. Positioning the reader against the substrate electrically couples the reader to the conductors to detect the presence of the liquid.

19 Claims, 9 Drawing Sheets

(56) References Cited

U.S. PATENT DOCUMENTS

| | | | | |
|---|---|---|---|---|
| 5,235,286 | A | 8/1993 | Masia | |
| 5,275,044 | A | 1/1994 | Riley | |
| 5,570,030 | A | 10/1996 | Wightman | |
| 5,698,083 | A | 12/1997 | Glass | |
| 6,175,310 | B1 | 1/2001 | Gott | |
| 6,787,718 | B2 | 9/2004 | Andberg | |
| 7,292,155 | B2 | 11/2007 | Vokey | |
| 7,688,215 | B2 | 3/2010 | Vokey | |
| 8,236,164 | B2 * | 8/2012 | Gustafsson .......... | G01N 27/223 204/430 |
| 2005/0165369 | A1 | 7/2005 | Hodge | |
| 2005/0225335 | A1 | 10/2005 | Filipkowski | |
| 2005/0255724 | A1 | 11/2005 | Picco | |
| 2009/0158819 | A1 | 6/2009 | Vincent | |
| 2009/0218223 | A1 | 9/2009 | Manaresi | |
| 2010/0127848 | A1 | 5/2010 | Mustapha | |
| 2010/0241094 | A1 | 9/2010 | Sherron | |
| 2010/0319435 | A1 | 12/2010 | Strong | |
| 2011/0179861 | A1 | 7/2011 | Grange | |
| 2012/0251859 | A1 | 10/2012 | Payne | |
| 2013/0075018 | A1 | 3/2013 | Heppe | |
| 2013/0150769 | A1 | 6/2013 | Heppe | |
| 2015/0233855 | A1 * | 8/2015 | Delie .................. | G01N 27/048 324/694 |

FOREIGN PATENT DOCUMENTS

| | | |
|---|---|---|
| EP | 563809 | 10/1993 |
| EP | 1751302 | 2/2007 |
| GB | 2218837 | 11/1989 |
| WO | 1989000681 | 1/1989 |
| WO | 2000000801 | 1/2000 |
| WO | 2006086178 | 8/2006 |
| WO | 2009018650 | 2/2009 |
| WO | 2010064753 | 6/2010 |

* cited by examiner

METHODS AND APPARATUS FOR A MOISTURE DETECTOR

FIELD OF THE INVENTION

Embodiments of the present invention relate to moisture sensors and processing circuits that cooperate with the moisture sensors to detect the presence of moisture.

BRIEF DESCRIPTION OF THE DRAWING

Embodiments of the present invention will be described with reference to the drawing, wherein like designations denote like elements, and.

DETAILED DESCRIPTION OF THE PREFERRED EMBODIMENTS

Figure 1:
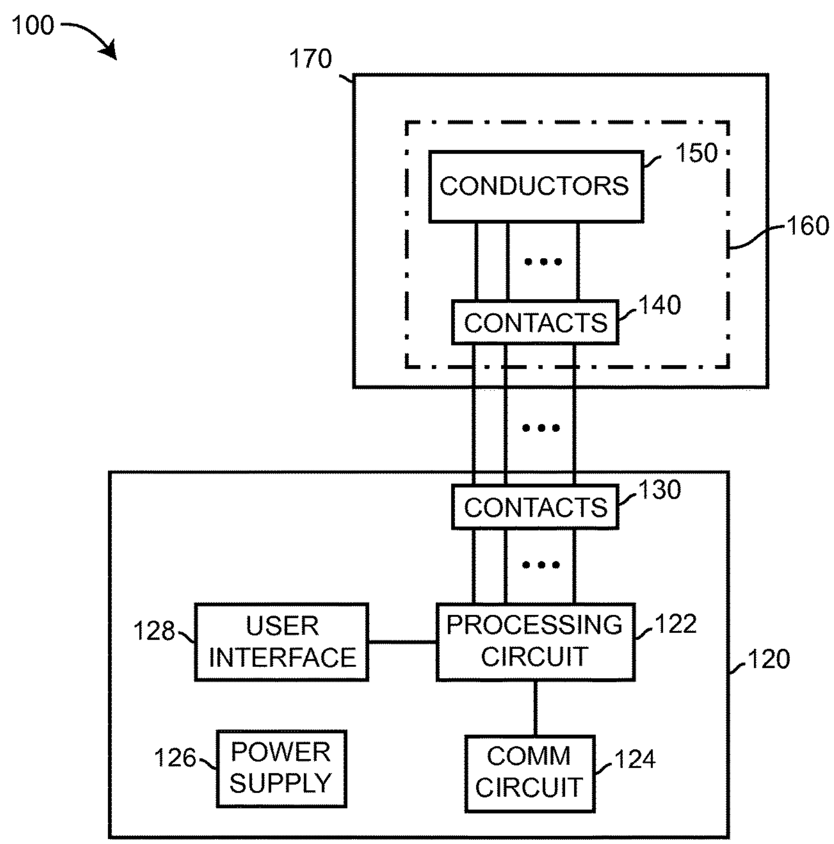
FIG. 1 is a functional diagram of a moisture detector according to various aspects of the present invention.

A moisture detector may include a moisture sensor and a reader. A moisture detector may detect the presence (e.g., existence, occurrence) of moisture (e.g., liquid, salt water, urine, blood). A moisture sensor may cooperate with a reader so that the reader may detect the position and/or spread (e.g., extent, area) of a liquid with respect to the moisture sensor, the conductors of the moisture sensor and/or a substrate (e.g., pad, layer) on which (e.g., in, under) the moisture sensor is positioned.

The physical structure of a moisture sensor may cooperate with the physical structure of a reader so that the reader may removeably couple to the moisture sensor. A moisture sensor may be integrated into a substrate such that coupling a reader to the substrate further couples the reader to the moisture sensor. A reader may be removed from a substrate/moisture sensor so that it may be reused by coupling it to a different substrate/moisture sensor. A reader may detect when it is properly (e.g., electrically, mechanically) coupled to a moisture sensor. A reader may detect an initial state of a moisture sensor and/or substrate prior to the introduction of moisture into the moisture sensor and/or substrate.

The substrate and moisture sensor may be formed of flexible materials so that prior to deployment, the substrate and moisture sensor may stowed (e.g., stored) in a compacted (e.g., rolled up, folded) form. The substrate and/or moisture sensor, in whole or in part, may be form of a rigid material such that the length prior to deployment and after deployment is substantially the same. The substrate and moisture sensor may be manufactured in standard lengths for deployment. The substrate and moisture sensor may be manufactured for deployment in variable lengths. Couplers may be used to couple two or more lengths of substrate/moisture sensor. Couplers may further be used to facilitate coupling a reader to a substrate/moisture sensor.

For example, moisture detector 100 includes reader 120 and moisture sensor 160. Moisture sensor 160 may be coupled to, positioned on, and/or integrated into pad 170. Pad 170 may include one or more layers of material. One or more layers of pad 170 may absorb or repel moisture. Moisture sensor 160 may be coupled to, positioned on, and/or integrated into one or more of the layers of pad 170. One layer of pad 170 may be referred to as a substrate. Moisture sensor 160 may be coupled to the substrate of pad 170. A substrate may be formed of an absorbent or non-absorbent material. Moisture sensor 160 or at least conductors 150 may be covered (e.g., positioned on, positioned over, positioned on top of) by an absorbent layer (not shown in FIGS. 1-4). This absorbent layer may be referred to as a cover. Pad 170 may include a non-absorbent base layer. Pad 170 and conductors 150 may have any shape for a particular application, for example, the shape of a diaper. Moisture sensor 160 may be coupled to, positioned on, and/or incorporate into a portion of pad 170 or most of the area of pad 170.

A cover may be formed of a material (e.g., dielectric) that when dry does not conduct electricity. However, the liquid absorbed by a cover may be conductive so that the liquid conducts a current.

A reader may detect the presence of a liquid in a moisture sensor and/or the substrate. A reader may detect a position of a liquid along a length of a conductor and thereby the position of the liquid with respect to the moisture sensor. The area of a moisture sensor may correlate to the area of a substrate, so determining the position of a liquid with respect to the moisture sensor means that the position of the liquid may be correlated to a location on the substrate. A reader may detect an area of the spread of a liquid with respect to the moisture sensor, so determining the spread of the liquid may be correlated to an area of the liquid on the substrate.

A reader may detect a current flow through a circuit and/or a voltage across a circuit that includes some or all of a conductor, a contact, the substrate, and/or the liquid positioned in the substrate. A reader may electrically and mechanically couple to one or more conductors of the moisture sensor or contacts thereof. A reader may apply a voltage across one or more conductors. A reader may detect a current flow through a conductor, a substrate, and/or a liquid. A reader may detect an impedance (e.g., resistance) of a conductor, a liquid, a substrate and/or a combination thereof.

A reader may determine a physical property of a conductor, a substrate and/or a liquid. A physical property may include capacitance, inductance, temperature, and impedance. For example, a reader may determine a physical property of a liquid, a substrate, a conductor, or a combination of the liquid and the substrate.

A reader, for example reader 120 of FIG. 1, may include contacts 130, processing circuit 122, communications ("comm") circuit 124, power supply 126, and user interface 128.

A power supply may provide energy for operation of the reader. A power supply may provide electrical energy for the operation of the components (e.g., processing circuit 122, comm circuit 124, user interface 128) of a reader. A power supply may provide electrical energy for application to and/or across one or more conductors, the substrate, and/or a liquid. A power supply may provide electrical energy having known characteristics (e.g., voltage magnitude, current magnitude, frequency, slew rate, pulse rate). A power supply may convert electrical energy so as to change the characteristics of the electrical energy provided. For example, a power supply may convert electrical energy provided at a lower voltage to electrical energy provided at a higher voltage. A power supply may covert energy provided as a direct current into energy provided as an alternating current. A power supply may include any conventional power supply technology including battery technology.

A processing circuit may electrically couple to one or more conductors of a moisture sensor. A processing circuit may control the provision of a current and/or voltage to a moisture sensor. A processing circuit may detect a voltage across and/or a current through a moisture sensor or a portion thereof. A processing circuit may detect a current that flows through one or more conductors of a moisture sensor, a substrate, and/or a liquid. A processing circuit may detect a voltage applied across one or more conductors of a moisture sensor, a substrate, and/or a liquid. A processing circuit may record, store, manipulate, and/or report a magnitude of a detected current and/or voltage. A processing circuit may include any conventional circuit for providing, controlling, converting, measuring, and/or detecting a voltage and/or a current. A processing circuit may control a power supply for providing a current and/or a voltage to the moisture sensor.

A processing circuit may perform any conventional type of calculation (e.g., add, subtract, multiply, divide, integrate, compare) and/or conversion (e.g., AtoD, DtoA, scale, invert). A processing circuit may store information. A processing circuit may detect, measure, and/or report physical properties (e.g., temperature, voltage, current, time, slew rate). A processing circuit may perform a calculation using detected, measured, previously calculated, and/or stored information. A processing circuit may receive information from a source outside of a reader (e.g., user, database, moisture sensor manufacturer) and use such information in any calculation and/or operation. A processing circuit may receive information from a source outside of the reader via a comm circuit. A processing circuit may report (e.g., provide) a result of detecting, calculating, and/or converting. A processing circuit may provide a result to a source outside the reader via a comm circuit. A processing circuit may perform a function in accordance with a result of calculating, converting, measuring, and/or detecting.

A processing circuit may include any conventional circuit for performing the functions of a processing circuit including converters, sensors, microprocessors, signal processors, relays, op amps, and comparators. A processing circuit may execute a stored program to perform the functions of the processing circuit. The execution of a stored program by a processing circuit may perform the functions of a reader.

A comm circuit may communicate (e.g., transmit, send, receive) electronically. A comm circuit may send information (e.g., data) and/or receive information electronically. A comm circuit may use any conventional protocol and/or circuits for communicating. A comm circuit may communicate via any conventional network (e.g., internet, WAN, LAN). A comm circuit may receive information for controlling a reader and/or the operations performed by the reader. A processing circuit may receive information from a comm circuit. A processing circuit may perform a function in accordance with information received via a comm circuit. A processing circuit may provide information for transmission to a comm circuit. A processing circuit may control the operation of and/or cooperate with the comm circuit to perform the functions of communication. A processing circuit may perform all or some of the functions of a comm circuit.

A processing circuit may provide a report. A report may include an electronic notice, an audible sound, a flashing light, and/or a printed message. An electronic notice may include a packet of data for communication via a conventional network, a text message for communication via a conventional cell phone network, and/or an electronic signal that conveys information. Subject matter of a report may include a notice of detected moisture; a notice of no detected moisture; a notice of a fault of the reader; a notice of proper electrical coupling of a reader to a moisture sensor, a position of detected moisture relative to a moisture sensor, a position of detected moisture relative to a substrate, an area of detected moisture and/or a status (e.g., energy level) of a power supply. A report may be provided to a comm circuit for transmission.

A contact provides a surface for mechanical and/or electrical coupling. A contact of a moisture sensor may electrically couple to a conductor of the moisture sensor for providing electrical energy to a conductor. A contact of a moisture sensor may mechanically couple to a substrate or to any layer positioned over and/or under the conductors of a moisture sensor. A reader may include contacts (e.g., prongs, teeth) for coupling to the contacts of a moisture sensor.

A reader may mechanically and/or electrically couple to a moisture sensor. A reader may mechanically couple to a substrate to establish a mechanical and/or electrical coupling with a moisture sensor. Contacts of a reader may mechanically and/or electrically couple to contacts of a moisture sensor. In the absence of contacts on a moisture sensor, a reader may directly mechanically and/or electrically couple to the conductors of a moisture sensor. A reader may removeably (e.g., detachably) couple to a substrate and/or a moisture sensor. A processing circuit may electrically couple to a moistures sensor via the coupling of the reader to the moisture sensor.

Moisture sensor 160 may include conductors 150 and contacts 140. Conductors 150 may include two or more conductors. Contacts 140 may include three or more contacts. Conductors 150 and contacts 140 may conduct an electrical current. At least two contacts are electrically coupled to one of the conductors preferably one contact at each end of the conductor. Contacts 140 may be positioned at any location on pad 170. Preferably, contacts 140 are positioned proximate to each other in the vicinity of an edge of pad 170 to facilitate coupling to reader 120. Conductors 150 cooperate with pad 170 to detect the presence of moisture. Contacts 140 cooperate with reader 120 for removeably coupling reader 120 to pad 170 and/or moisture sensor 160. Reader 120 electrically couples to moisture sensor 160 to detect whether moisture is present in moisture sensor 160 and/or in pad 170. A reader may report, electronically, audibly, and/or visually, a result of detecting.

Moisture sensor 260 of FIGS. 2-5 includes an implementation of conductors, contacts, and a substrate. Substrate 270 performs the functions of a substrate discussed herein. Substrate 270 includes an absorbent material for absorbing a liquid. Substrate 270 receives and absorbs liquids. Substrate 270 may cooperate with an additional layer (e.g., 510) of absorbent material positioned over conductors 250 and 252 to absorb liquid.

As a portion of substrate 270 becomes saturate with liquid, the liquid spreads across substrate 270, so that the area of substrate 270 that holds liquid increases. Conductors 250-252 are integrated into or are mechanically coupled to substrate 270. As discussed in further detail below, the absorbent material of substrate 270 cooperates with conductors 250-252 to capture liquid in a manner that conductors 250-252 in cooperation with reader 120 may detect the presence of the liquid.

Mechanically coupling conductors 250 and/or 252 to substrate 270 may include using a conventional sewing machine to sew a conductive thread to substrate 270 so that the conductive thread performs the functions of conductors as discussed herein.

A conductor may be formed of any conductive material. Conductive material may include a metal and/or semiconductive (e.g., semi-conductor) material. The structure (e.g., form, length, height, width) of a conductor includes any conventional structure of a conductor. Structures of a conductor may include the form of a conventional wire, a thin-film conductor, a thick-film conductor, and a deposited (e.g., printed, formed by deposition) conductive material.

A conductor has an impedance (e.g., resistance). The impedance of a conductor may include the bulk resistivity of the material of the conductor (e.g., ρ, rho), sheet resistance of the material of the conductor, and a total resistance of the conductor.

Conductors whose impedance is described in terms of a sheet resistance may have a width, a thickness, a length (e.g., volume), and a bulk resistivity ρ (i.e., rho). Sheet resistance Rs is defined as the resistivity ρ divided by the thickness of the conductor. Sheet resistance is expressed as Ω/□ (i.e., ohms/square, ohms per square). In equation form, Rs is:

$$Rs=\rho/t, \qquad \text{Equation 1}$$

where:

ρ (e.g., rho) is the bulk resistivity of the conductor, as discussed above.

t is the thickness of the conductor.

Figure 3:
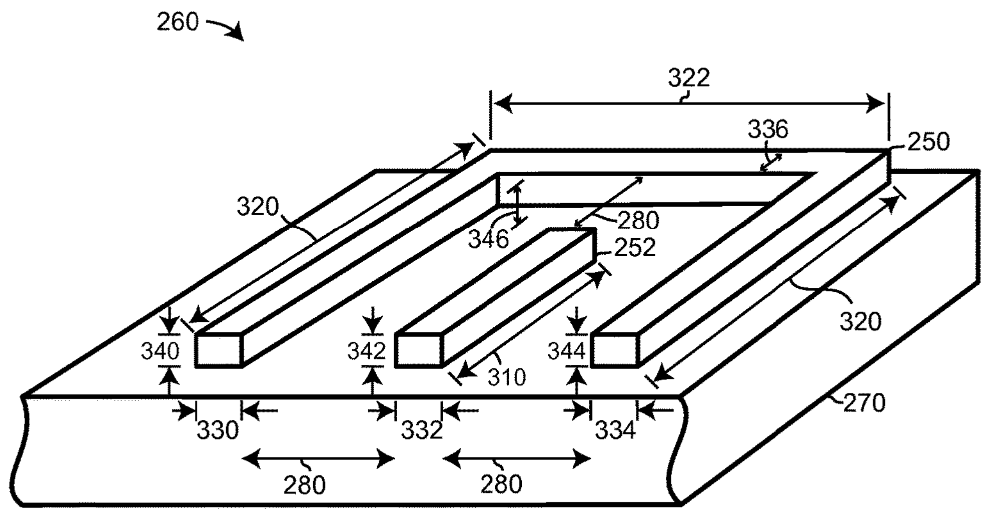
FIG. 3 is a perspective plan view of the substrate and conductors of FIG. 2.

An example of a conductor having a sheet resistance and a thickness shown in FIG. 3. Conductor 252 has width 332, thickness 342, and length 310. Conductor 250 includes three different sections. A first section of conductor 250 has width 330, thickness 340 and length 320. A second section has width 334, thickness 344, and length 320. A third section has width 336, thickness 346, and length 322. Some or all of widths 330, 334, 336; thicknesses 340, 344, and 346; and lengths 320 and 322 may be the same or different. The total length of conductor 250 is the sum of the lengths of its sections (i.e.: 320+320+322).

The impedance of a conductor having a sheet resistance or an impedance per unit length is proportional to a length of the conductor, so the total resistance of conductors 250 and 252 is proportional to their respective lengths.

A total resistance of a conductor may be determined (e.g., calculated) in accordance with the sheet resistance of the material of the conductor, a width of the material of the conductor, and a length of the material of the conductor. The total resistance of a conductor may be expressed as:

$$R=Rs*(L/W), \qquad \text{Equation 2}$$

where:

Rs is the sheet resistance of the material of the conductor, as provided above in Equation 1.

L is the length of the conductor.

W is the width of the conductor.

The total resistance of conductors 250 and 252 may be calculated as:

$$R252=Rs252*(\text{length }310/\text{width }332); \text{ and}$$

$$R250=(Rs250*(\text{length }320/\text{width }330))+(Rs250*(\text{length }320/\text{width }334))+(Rs250*(\text{length }322/\text{width }336)).$$

Rs252 is the sheet resistance of the material that forms conductor 252. Rs250 is the sheet resistance of the material that forms conductor 250. For the sake of simplicity, assume that all sections of conductor 250 are formed of the same material so that the sheet resistance of the material of each section is the same. The material of conductor 250 may be different from the material of conductor 252, so sheet resistance Rs250 may be different from sheet resistance Rs252.

R252 is the total impedance of conductor 252 along its entire length, which is length 310. R250 is the total resistance of conductor 250 along its entire length, which is length 320+length 320+length 322.

The total impedance (e.g., resistance) of a conductor may also be determined using the relationship V=IR. A voltage of a known magnitude may be applied across a conductor. The current provided through the conductor by the source of the voltage may be measured. The total resistance of the conductor may be calculated as R=V/I. Alternatively, a current of a known magnitude may be provided through the conductor and the magnitude of the voltage across the conductor measured. The total resistance of the conductor may be calculated using the above formula.

According to various aspect of the present invention, the material and/or structure (e.g., width, thickness, length) of conductor 250 is different from the material and/or structure of conductor 252 so that the total impedance of conductor 250 is different from the total impedance of conductor 252. Preferably, the total impedance of conductor 250 is greater than the total impedance of conductor 252. The difference in impedance may result from not only from differences in structure, but also in differences in bulk resistivity because the conductors are formed of different materials (e.g., Al, Cu, C).

Preferably, the sheet resistance of conductor 250 is greater than the sheet resistance of conductor 252 so the per square impedance of conductor 250 is greater than the per square impedance of conductor 252. In an implementation, the impedance per square of conductor 250 is greater than the impedance per square of conductor 252. In another implementation, the impedance per square of conductor 250 is at least two to three times greater than the impedance per square of conductor 252. In another implementation, the impedance per square of conductor 250 is at least five to ten times greater than the impedance per square of conductor 252. Further, the total resistance of the entire length of conductor 250 is greater than the total resistance of the entire length of conductor 252.

The impedance per square of conductor 250 may also be greater than the impedance of any liquid that may be absorbed by substrate 270 so that the liquid is positioned between and contacting conductor 250 and 252.

Figure 4:
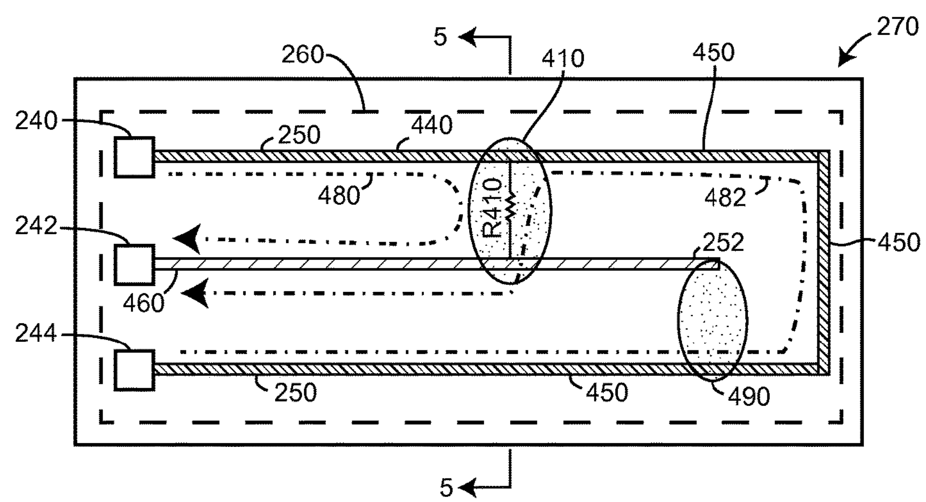
FIG. 4 is the top plan view of FIG. 2 with liquid present and indicators of electrical loops.
Figure 5:
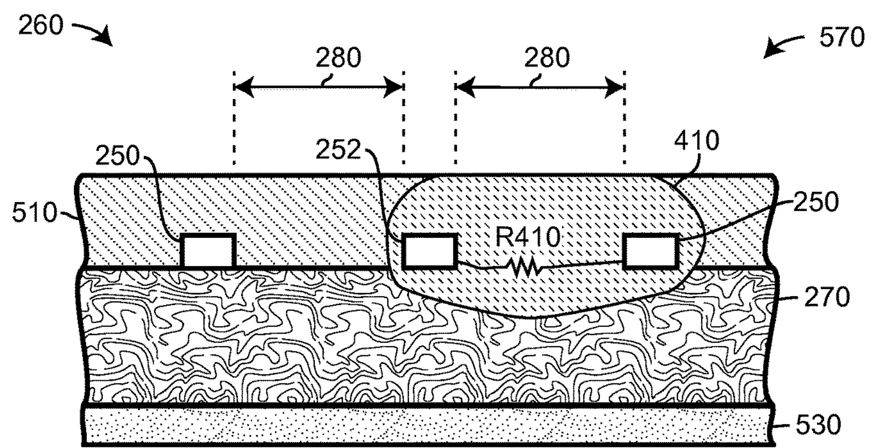
FIG. 5 is a cross section of the moisture sensor of FIG. 4 at 5-5.

For example, referring to FIGS. 4 and 5, liquid 410 has been absorbed, at least partially, by substrate 270 so that liquid 410 is positioned between (e.g., across, bridging) conductor 250 and 252. Liquid 410 is conductive so it functions as impedance R410 between conductor 250 and 252. The magnitude of impedance R410 depends on the distance between conductors 250 and 252 and the bulk resistance of the liquid between the conductors.

To aid in detecting liquid, the distance between conductors 250 and 252 is uniform along the lengths of the conductors. An exception at the interior corners of conductor 250 where conductor 250 turns at 90 degree angles. In this implementation, the distance between conductor 240 and conductor 252 ranges between one times the distance along a straight portion of the conductors and 1.414 (e.g., root 2) times the distance in the corners of conductor 250. Conductor 250 may be implemented as a semicircle so that the distance between conductor 250 and 252 is the same at all points along the conductors.

Distance 280 between conductors 250 and 252 sets a maximum value for R410 of a liquid having a particular bulk resistance. For example, if the distance between conductor 250 and 252 is one centimeter, the magnitude of resistance R410 will be between 150 and 400 ohms for a material having a bulk resistance of between 150-400 ohms-centimeter (i.e.: Ω-cm).

In another example, for a spacing (e.g., 280) of 0.2 centimeters between conductor 250 and 252, the magnitude of R410 for a liquid having a bulk resistance of between 150-400 Ω-cm would be in the range of 30 to 80 ohms. The sheet resistance of conductor 250 may be less than, equal to or greater than the bulk resistance of the liquid. For example, the sheet resistance of conductor 250 may be in the range of less than 1 ohms per square to 800 ohms per square. In an implementation, the sheet resistance of conductor 250 is 0.01 ohms per square. In another implementation, the sheet resistance of conductor 250 is 800 ohms per square.

In an implementation, the distance between conductors 250 and 252 is such that the maximum value of R410 is less than the resistance of the shortest portion of conductor 250 that a current may travel through before reaching impedance R410. For example, when a current travels loop 480, the current travels from contact 240 through portion 440 of conductor 250 before reaching impedance R410. The total resistance of portion 440 is greater than the magnitude of the impedance of R410. Liquid 410 may be positioned closer to contact 240, so the portion of conductor 250 through which the current travels may be much shorter than portion 440. Preferably, the distance between conductor 250 and 252 and the sheet resistance of conductor 250 ensures that the impedance of any portion of conductor 250 is at least five to ten times greater than the impedance of any liquid between conductors 250 and 252.

For example for this implementation, for a spacing (e.g., 280) of 0.2 centimeters between conductor 250 and 252, the magnitude of R410 for a liquid having a bulk resistance of between 150-400 Ω-cm would be in the range of 30 to 80 ohms. The sheet resistance of conductor 250 is in the range of 400 to 800 ohms per square, preferably 800 ohms per square.

In the same implementation, the impedance per square of conductor 252 may be less than the impedance of any liquid positioned between conductor 250 and 252. As discussed above, for a spacing of 0.2 centimeters between conductor 250 and 252, the magnitude of R410 for a liquid having a bulk resistance of between 150-400 Ω-cm would be in the range of 30 to 80 ohms. The sheet resistance of conductor 252 may be in the range of 3 to 8 ohms per square, preferably 3 ohms per square or less.

The spacing between conductor 250 and 252 may depend on the amount of liquid expected to be caught (e.g., captured, absorbed) by a particular substrate or the minimum amount of liquid that should be detected for a particular substrate or application. The relationship between the sheet resistance of conductors 250 and 252 and the spacing between the conductors discussed above may hold regardless of spacing.

The spacing between and sheet resistance of conductors 250 and 252 may be different for liquids that have different bulk resistance.

Reader 120 provides electrical signals and measures electrical signals to determine the portions of conductors 250 and 252 that lead to or from the impedance of a liquid positioned between conductors 250 and 252. Reader 120 may detect the length of the portion of conductor 250 and/or 252 between contacts 240-244 and impedance R410 of liquid 410. Determining the location of liquid 410 along the length of conductor 250 and/or 252 from contacts 240-244 provides information of the position of liquid 410 relative to conductors 250 and 252 and contacts 240-244. However, because the sheet resistance of conductor 250 is higher than the sheet resistance of conductor 252, reader 120 may more accurately determine the position of liquid 410 with respect to conductor 250 rather than conductor 252 because the change in impedance along conductor 250 is greater than the change in impedance along conductor 252 and therefor easier to detect (e.g., measure). Accordingly, because reader 120 may determine the length of the portion of conductor 250 between contact 240 and/or 244 and liquid 410, reader 120 may determine position of liquid 410 relative to conductor 250.

Figure 6:
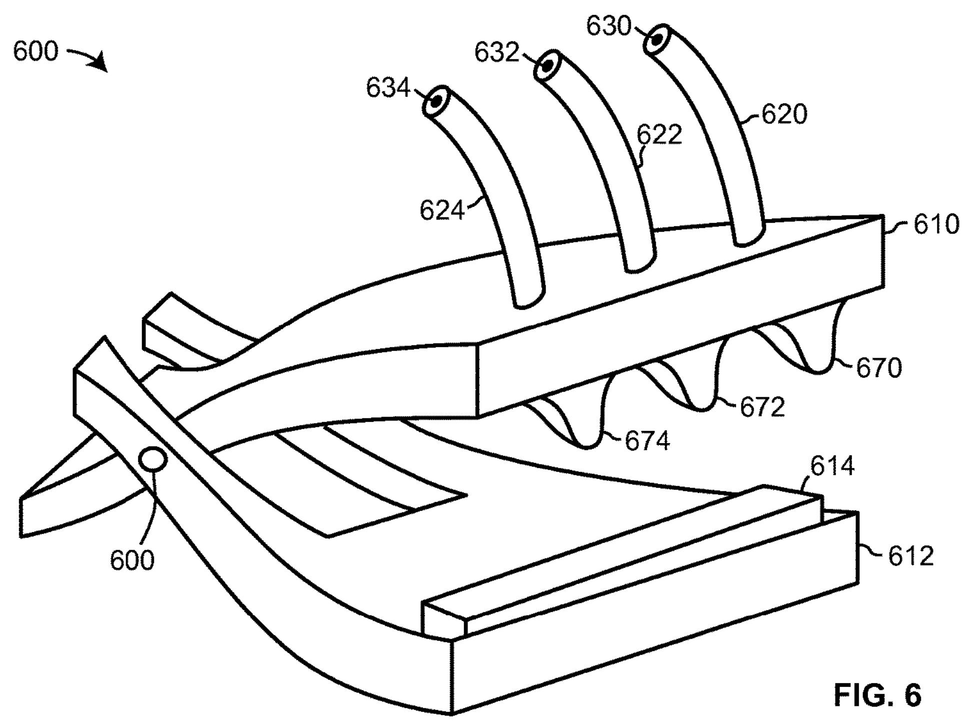
FIG. 6 is a plan perspective view of a clip for coupling to a moisture sensor according to various aspects of the present invention.

Reader 120 may include clip 600, shown in FIG. 6, for mechanically and electrically coupling to moisture sensor 260 and/or substrate 270. Clip 600 may include teeth 670-674 for coupling mechanically and electrically to contacts 240-244 of moisture sensor 260. Teeth 670-674 are formed of a conductive material so that teeth 670-674 may perform the function of contacts as discussed above. Support 614 may mechanically (e.g., friction, pressure) couple to substrate 270 to hold (e.g., maintain, retain) clip 600 mechanically and electrically coupled to substrate 270 and moisture sensor 260, in particular contacts 240-244. Clip 600 may include a resilient force (e.g., spring, magnet) that forcefully moves upper jaw 610 toward lower jaw 612 so that teeth 670-674 move toward and are maintained proximate to support 614. A force (e.g., pressure) between teeth 670-674 and support 614 may mechanically couple clip 600 to moisture sensor 260 and substrate 270. Physical contact of teeth 670-674 with contacts 240-244 (740-744, 940-944) may electrically couple teeth 670-674 to contacts 240-244 (740-744, 940-944). Clip 600 may include more than three teeth for substrates that have more than three contacts. Generally, clip 600 includes one tooth for each contact.

Preferably, contacts 240-244 (740-744, 940-944) are positioned proximate to each other and on the same edge of substrate 270 (770) or pad 570 (970, 1370), so that clip 600 may be compact and physically contact contacts 240-244 (740-744, 940-944) when coupled.

Electrical contact of a first tooth of clip 600 with contact 240 (740) and a second tooth of clip 600 with contact 244 (744) provides a circuit via conductor 250 (750) for reader 120 to determine that it is electrically coupled to moisture sensor 260 (760). Upon coupling reader 120 to moisture sensor 260, reader 120 may provide a voltage across contacts 240 and 244 not only to determine whether an electrical connection is established with conductor 250, but also to determine an initial resistance of conductor 250 prior to use of substrate 270 to absorb liquid.

The initial resistance of conductor 250 may be used to identify the version (e.g., model number, make) the moisture sensor. The initial resistance of conductor 250 may be measure by applying a voltage across contacts 240 and 244 and measuring the resulting current. A look-up table may be used to correlate the magnitude of the initial impedance of conductor 250 to a model number of the moisture sensor. As shown here, the physical layout (e.g., shape, width, length) of the conductors may be different for various types of moisture sensors. Knowledge of the layout of a moisture sensor may provide information to permit correlation of the position of a liquid with respect to a conductor to a position with respect to the substrate and/or cover of the moisture sensor. Knowledge of the layout of the moisture sensor may provide information for interpreting the voltages and currents measured from the moisture sensor.

The initial value of conductor 250 may be unique, within a range, for each different version of moisture sensor. A reader may detect the initial value and correlate the initial value to information for reading and interpreting electrical and physical information about the moisture sensor. A reader may store such information for a variety of moisture sensors or the reader may transmit the initial value of conductor 250 to a server and receive information that corresponds to that version of the moisture sensor. A reader may provide (e.g., transmit) the version number of the moisture sensor. A reader may provide the version number of the moisture sensor each time it transmits information gathered by the reader so that the information may be construed in light of the version of the moisture sensor.

The physical structure of teeth 670-674 of clip 600, including absolute teeth position, teeth position relative to each other, length, and width. Teeth 670-674 may be positioned relative to each other and relative to contacts 240-244 so that the proper placement of any two teeth in contact with two contacts of contacts 240-244 guarantees that the other tooth is properly coupled to its respective contact. For example, tooth 672 is positioned between teeth 670 and 674. While reader 120 is properly coupled to contacts 240-244, reader 120 may detect an electrical connection between teeth 670 and 674 via conductor 250. Because of the physical placement of tooth 672 between teeth 670 and 674, confirmation of proper electrical coupling of teeth 670 and 674 by reader 120 guarantees that tooth 672 is properly coupled to contact 242.

Conductor spacing and/or position of contacts, whether three or more, may be standardized for many types of substrates so that the same clip may be used to contact to all of the substrate types.

Clip 600 includes pin 640 so that upper jaw 610 may be rotated away from lower jaw 612 so that clip 600 may be decoupled, both electrically and mechanically, from moisture sensor 260 (760) and substrate 270 (770) or pad 570 (970, 1370). The force that moves upper jaw 610 toward lower jaw 612 to couple clip 600 to moisture sensor 260 (760) and substrate 270 (770) or pad 570 (970, 1370) must be overcome to move upper jaw 610 away from lower jaw 612 to release clip 600 from moisture sensor 260 (760) and/or substrate 270 (770) or pad 570 (970, 1370).

Teeth 670-674 may couple to conductors 630-634 of wires 620-624 respectively. Wires 620-624 may couple to processing circuit 122 so that reader 120 is electrically coupled to moisture sensor 260 so that reader 120 may perform the functions of a reader discussed herein. Reader 120 may be small enough in size that reader 120 may be integrated with clip 600 so that wires 620-624 are short or replaced by some other type of electrical connection between processing circuit 122 and teeth 670-674 that is suitable for a circuit integrated into clip 600.

Clip 600 may have additional teeth for proper coupling to a type of moisture sensor that has additional contacts. It is also possible to have a clip with more teeth than contacts on a particular type of moisture sensor. A subset of the teeth may couple to the contacts of the moisture sensor. In the implementations discussed, clip 600 has one tooth for each contact of a moisture sensor. Because contacts may be positioned on top of a substrate and/or the bottom of a substrate, clip 600 may have teeth on upper jaw 610 and/or lower jaw 612.

While reader 120 is electrically coupled to moisture sensor 260, using clip 600 or any other type of conventional coupler, reader 120 may determine whether liquid is present on substrate 270 (770) or pad 570 (970, 1370) and the location of the liquid with respect to at least conductor 250 (750, 910/912, 1410/1414) and thereby with respect to substrate 270 (770) or pad 570 (970, 1370).

Referring to FIGS. 2-5, to detect moisture 410 on substrate 270, reader 120 may provide voltages across contacts 240-244, detect currents, and use information about the magnitudes of the currents and/or the voltages to determine a magnitude of an impedance of moisture sensor 260. The detected impedance of moisture sensor 260 relates to whether moisture is present or absent from moisture sensor 260. The magnitudes of the impedances further related to the position of liquid 410 with respect to conductors 250 and 252, and in particular with respect to conductor 250. If there is some type of known correlation between the position of conductors 250 and/or 252 to substrate 270, reader 120 may further correlate the position of moisture 410 to a position on substrate 270.

In an implementation, reader 120 may perform the following operations to detect moisture 410 and to determine the position of moisture 410 relative to conductors 250 and/or 252. In this example, assume that liquid 490 is not present. Reader 210 applies a voltage across contacts 240 and 242 to induce a current through loop 480. Because the impedance per square of conductor 250 is greater than the impedance per area of moisture 410, any current provided by reader 120 travels along portion 440 of conductor 250 until it reaches the lower impedance of moisture 410. The current traverses R410 of moisture 410 to the even lower impedance of conductor 252. The current returns to reader 120 along portion 460 of conductor 252. Reader 210 calculates the impedance (e.g., magnitude of impedance) of loop 480.

The distance 280 between conductors 250 and 252 is known by reader 120. Further, reader 120 has information as to the range of impedances of the liquids that might be present in substrate 270. Knowing the distance between conductors 250 and 252, reader 120 may determine (e.g., calculate) a range of impedances for R410. The impedance of R410 may be subtracted from the total impedance of loop 480 to determine the resistance of portion 440 of conductor 250 and portion 460 of conductor 252; however, since the impedance of conductor 252 is much lower than the impedance of conductor 250, the impedance that remains after the impedance of R410 is subtracted is predominantly the impedance of portion 440 of conductor 250.

Reader 210 applies a voltage across contacts 242 and 244 to induce a current through loop 482, again assuming that liquid 490 is not present. Because the impedance per square of conductor 250 is greater than the impedance per area of moisture 410, any current provided by reader 120 travels along portion 450 of conductor 250 until it reaches the lower impedance of moisture 410. The current traverses R410 of moisture 410 to the even lower (e.g., lesser) impedance of conductor 252. The current returns to reader 120 along portion 460 of conductor 252. Reader 210 calculates the impedance of loop 482.

As discussed above, the reader has calculated a range of impedances for the likely liquids in substrate 270. The impedance from R410 may be subtracted from the impedance of loop 482 to determine the impedance of portions 460 and conductor 252 and 450 of conductor 250. Because the impedance per square of conductor 250 is higher than the impedance per square of conductor 252, the impedance after subtracting R410 is predominantly the impedance of portion 450 of conductor 250.

As discussed above, the majority of the magnitude of the impedance of loop 480 and 482 is due to the impedance of conductor 250. Reader 210 may use the ratio of the impedance of loop 480 to the total initial impedance of conductor 250 to determine the distance from contact 240 to the position of moisture 410. Reader 120 may also use the ratio of the impedance of loop 480 and loop 482 after subtraction to the total initial impedance of conductor 250 to find the distance of liquid 410 from contacts 240 and 244 respectively.

For example, if the ratio of the impedance of loop 480 or portion 440 to the total initial impedance of conductor 250 is about 0.25, then the position of moisture 410 is about a quarter of the total length of conductor 250 from contact 240. The length of portion 440 is about one-quarter of the total length of conductor 250. If the ratio of the impedance of loop 482 or portion 450 to the total initial impedance of conductor 250 is about 0.75, then the position of moisture 410 is about three-quarters of the total length of conductor 250 from contact 244. The length of portion 450 is about three-quarters of the total length of conductor 250.

The position of liquid 410 along the length of conductor 250 from contacts 240 and 244 provide information as to the position of liquid 410 with respect to conductor 250 and contacts 240 and 244.

The width, or spread, of moisture 410 may be determined by detecting the difference between the position of moisture 410 from contact 240 and the position of moisture 410 from contact 244. For example, if the distance from contact 240 and from contact 244 to moisture 410 is about 25% and 45% of the length conductor 250 respectively, moisture 410 has spread along about 20% of the length of conductor 250. It is also possible that moisture 410 is positioned at the 25% point from contact 240 and moisture 490 is positioned at the 45% point from 244 with no liquid in between liquid 410 and liquid 490.

The initial impedance of conductor 250 may be detected by reader 120 while reader 120 is coupled to moisture sensor 260 at contacts 240-244 prior to deployments of moisture sensor 260 or prior to absorbing any liquid by substrate 270. Another method for determining the initial impedance of conductor 250 is for the impedance to be measured and/or characterized at manufacture and such information provided to reader 120 for example via comm circuit. The magnitude of the initial impedance may be recorded by reader 120 whether it is measured by reader 120 or provided to reader 120. Reader 120 may use the stored initial impedance to perform calculations such as detecting the position and/or spread of moisture as discussed herein.

Reader 120 may calculate and record, from time-to-time, the position and spread of liquid 410. Reader 120 may use historical information to determine a rate of spreading. Reader 120 may provide a notice in accordance with a rate of spread as to a possible time that substrate 270 may need to be replaced. The notices provided by reader 120 may be routed to a care giver to provide the care giver information as to when substrate 270 may need to be changed due to the amount and/or spread of liquid in substrate 270. Reader 120 may provide an estimated time of day, in accordance with an calculated rate of spread, when the substrate (e.g., pad) should likely be changed.

Because the sheet resistance of conductor 250 is higher than the impedance per area of the liquid and the sheet resistance of conductor 252, the impedance of a loop (e.g., 480, 482) relates more directly to impedance of the portion of conductor 250 in the loop than to the impedance of the liquid or the impedance of the portion of conductor 252 in the loop. Further, as discussed above, the estimated impedance of the liquid may be subtracted from the impedance of a loop to provide a resulting impedance that is more closed related to the impedance of the portion of conductor 250 in the loop.

Because the impedance of conductor 250 is measured from both end portions of conductor 250 via loop 480 and 482, the edges of moisture 410 may be detected and related to a length along conductor 250. If the length of conductor 250 relates to positions on substrate 270, the measurements with respect to conductor 250 from contact 240 and 244 may relate to positions on substrate 270, and therefore to an area of substrate 270.

Conductors may mechanically couple to a substrate. The spacing between conductors may be uniform and/or variable. Preferably, the spacing between conductors is uniform so that reader 120 may estimate the impedance of potential liquids between conductors. However, because reader 120 can detect a distance along a conductor to a position of a liquid, reader 120 may also use stored information to look up the distance between the conductors at the position of the liquid. Knowing the distance between the conductors at the position of the liquid enables reader 120 to estimate the impedance of the liquid at that position. So, reader 120 may estimate the impedance of a liquid even though the distance between the conductors varies. As discussed above, conductor spacing may relate to the conductive properties of a liquid so that that the impedance through a liquid between conductors is within a desired range.

The properties of the material used to form a substrate may promote a uniform (e.g., even) spread of a liquid through the substrate and around (e.g., between) the conductors. The absorbency of a substrate may promote uniform spread of a liquid across the substrate and around conductors as opposed to the liquid reaching a conductor and flowing nearly exclusively along the length of the conductor.

A substrate may be a part of a pad that encloses (e.g., envelopes) a moisture sensor. A pad may be formed of layers of materials. The layers of the materials may be the same and/or different. One or more layers of a pad may be sterile. A conductor of a moisture sensor may be positioned in or on the substrate of a pad, another layer, or alternate between layers. A pad may include one or more layers that cover the substrate and/or conductors of the moisture sensor. The one or more layers may be referred to as a cover. Any number of layers may be positioned above and/or below the conductors of the moisture sensor. Conductors of a moisture sensor may be positioned on the same side of the same layer, different sides of the same layer, or on different layers of the pad. A conductor may couple (e.g., affix, attach, fasten, connect) to the substrate or any layer of a pad using any conventional method (e.g., printing, deposition, mechanical, adhesive, sewing). A substrate or any other layer of a pad may insulate the conductors from each other in the absence of a liquid.

A layer of a pad may absorb or resist the penetration of liquid. A layer may facilitate the uniform spread of a liquid through the pad and/or substrate. A material of a layer may retard the movement (e.g., spread) of a liquid. A layer may influence (e.g., direct, channel) the movement of a liquid through and/or across the pad and/or substrate. A layer may facilitate movement of a liquid toward and/or between conductors.

A layer of a pad may be formed of an absorbent and/or a non-absorbent material. A layer formed of a non-absorbent material may perform the function of retaining liquids in the pad as opposed to allowing the liquids to exit (e.g., leak from) the pad. A layer may function as an insulating layer for applications that may benefit from an insulated pad. A layer may perform the function of a protective barrier. A pad may be disposable after use.

A layer of a pad may provide a surface for mounting electronic circuits, conductors for power, an antenna for communication, and/or data buses associated with a moisture sensor and/or a reader. A layer of a pad provides a surface for the mounting of contacts for coupling to a reader. A layer of a pad may include a non-absorbent layer (e.g., polyethylene terephthalate, biaxially-oriented polyethylene terephthalate, mylar, melinex, hostaphan) to which the conductors, contacts, and any associated electronics are coupled. An absorbent layer may be placed over the non-absorbent layer.

Figure 2:
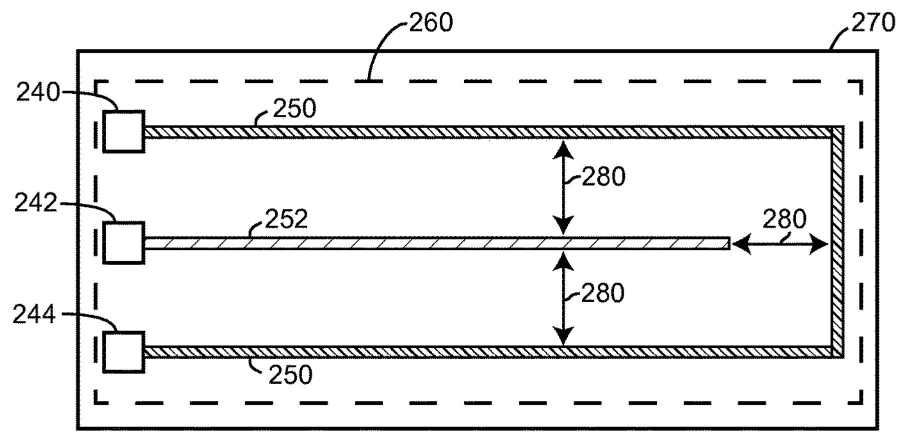
FIG. 2 is a top plan view of an implementation of a moisture sensor according to various aspects of the present invention.

For example, the pad of FIGS. 2-4 is shown as including a single layer substrate 270. The substrate 270 is positioned under conductors 250 and 252. No layer is shown as positioned over the conductors. Omitting a layer over conductors 250 and 252 simplifies the drawing for description, but may not be suitable for a substrate in actual use. An additional layer may be added to substrate 270 that covers conductors 250 and 252, such as cover 510. Such a layer may be absorbent. Cover 510 may be non-conductive when it has not absorbed a liquid. Pad 570 further includes base 530 under substrate 270. Base 530 may be non-absorbent so that liquid absorbed by substrate 270 and cover 510 does not exit pad 570.

Conductors of a moisture sensor may be laid out and/or positioned on a layer of a pad in any pattern. Regardless of the pattern, the principles discussed above for detecting the position and spread of moisture with respect to the conductors of the moisture sensor apply. Generally, as discussed above, it is a simplifying practice to keep the spacing between the conductors of the moisture sensor equally spaced from each other along their lengths, but as further discussed above constant spacing is not a requirement. Further, as discussed below, it is possible to protect portions of a conductor from moisture (e.g., waterproof) in areas where it is undesirable for liquid to create a circuit using those portions of the conductors. Conductors of a moisture sensor may further be laid out in a pattern that divides a substrate into zones.

For example, conductors 750 and 752 of moisture sensor 760 are arranged on a surface of substrate 770 in a serpentine pattern. Contacts 740-742 are positioned along the same edge of substrate 770 proximate to each other and perform the functions and include the characteristics of contacts 240-244 discussed above. Conductors 750 and 752 perform the functions and include the characteristics of conductor 250 and conductor 252 discussed above. Moisture sensor 760 performs the functions of a moisture sensor discussed above. Substrate 770 performs the functions of a substrate discussed above. Substrate 770 may be a part of a pad that includes additional layers as discussed with respect to substrate 570 such as an absorbent layer positioned over conductors 750 and 752 and a non-absorbent layer positioned under substrate 770.

Substrate 770 includes water (e.g., liquid, moisture) resistant layer (e.g., covering) 771. Layer 771 covers a portion of conductor 750 and substrate 770 so that moisture cannot bridge between the portion of conductor 750 that is covered by layer 771 and an adjacent portion of conductor 750. Covering portions of conductors 750 and 752 with layer 771 shields them from moisture so that moisture detection is accomplished in the areas of substrate 770 that are not protected (e.g., shielded) by layer 771. Layer 771 defines inactive portions of moisture sensor 760 while the portions of moisture sensor 760 not covered by layer 771 are the active portions of moisture sensor 760. Preferably, moisture cannot be detected in inactive portions, while moisture may be detected in active portions.

The serpentine pattern of conductors 750 and 752 divide substrate 770 into zones. The vertical, with respect to the orientation of FIGS. 7 and 8, portions of conductors 750 and 752, define zones 720-726. Zones may be used to relate the position of a liquid along conductors 750 and 752 to an area of substrate 770. A reader may include information that translates the position of the liquid with respect to conductors 750 and 752 into information regarding the zone where liquid is positioned. Substrate 770 may include indicia for an operator to relate zone information reported by a reader to the physical layout of substrate 770. For example, each zone of substrate 770 may have a different identifying color or printed indicator on the outside of substrate 770 so that an operator may identify the zone where liquid is detected by the reader. An operator may use zone information as related to substrate 770 to determine the extent of the spread of the liquid.

Reader 120 may use the same techniques discussed above for detecting the position of moisture with respect to conductors 750 and 752. As discussed above, reader 120 may provide a voltage across contacts 740-744 and detect the currents induced in loops 780 and 782 along conductors 750 and 752 and through impedance R710 of moisture 710. As discussed above, the magnitude of the impedance of loop 780 may be compared to the total magnitude of the initial impedance of conductor 750 to determine the position of moisture 710 with respect to conductor 750. Reader 120 may correlate the position of moisture 710 to a zone.

Because of the water resistant nature of layer 771, the path through contact 740 to moisture 710 will always be longer than the path through contact 744 to moisture 710. Reader 120 may have stored information regarding the physical layout of conductor 750 and the portions covered by layer 771, so that it may determine the position of moisture 710. An operator may provide the model number of a substrate to reader 120, so reader 120 may use stored information regarding the substrate for position, spread, and zone calculations.

Figure 7:
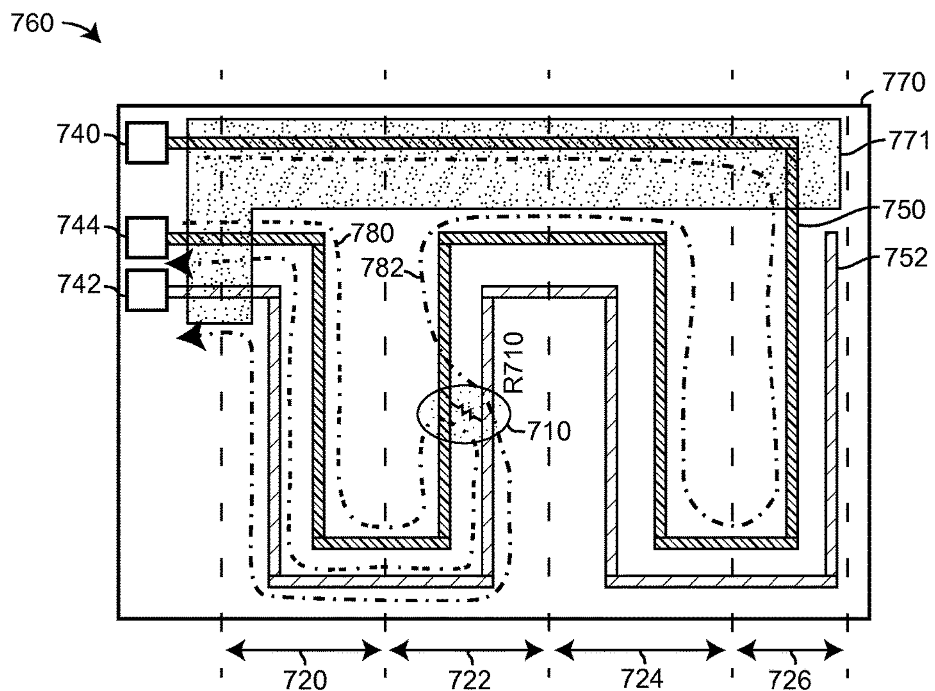
FIG. 7 is a top plan view of another implementation of a moisture sensor with liquid and electrical loops indicated.
Figure 8:
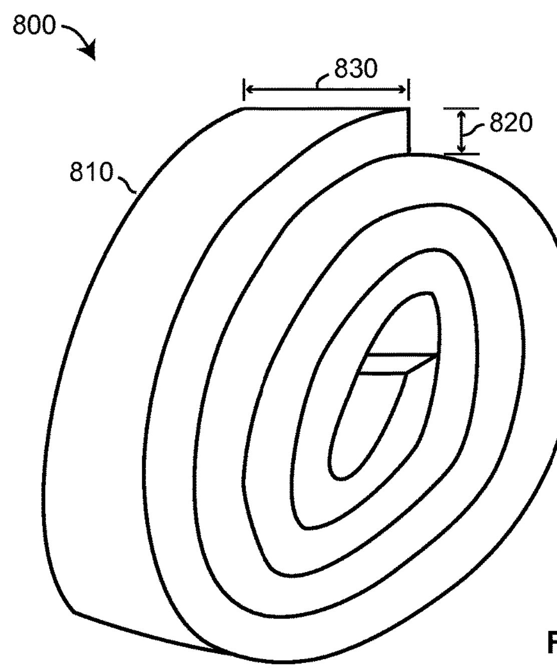
FIG. 8 is a plan view of another implementation of a moisture sensor positioned in a roll prior to deployment according to various aspects of the present invention.

In the implementation of FIG. 7, the spacing between conductor 750 and conductor 752 is uniform along the lengths of the conductors.

In an implementation, pad 170 containing moisture sensor 160 may be deployed (e.g., positioned) in an area where moisture may cause significant damage, but areas that are checked infrequently, such as under a sink, or areas that are difficult to access, such as under an appliance (e.g., washing machine, refrigerator).

For example, sensor roll 800 includes pad 810 that may be rolled around itself like a roll of masking tape prior to deployment, for storage, and/or for shipping. One side of pad 810 may include an adhesive for retaining pad 810 in the rolled shape prior to use and/or for retaining pad 810 in position when unrolled and placed in position to detect moisture.

Figure 9:
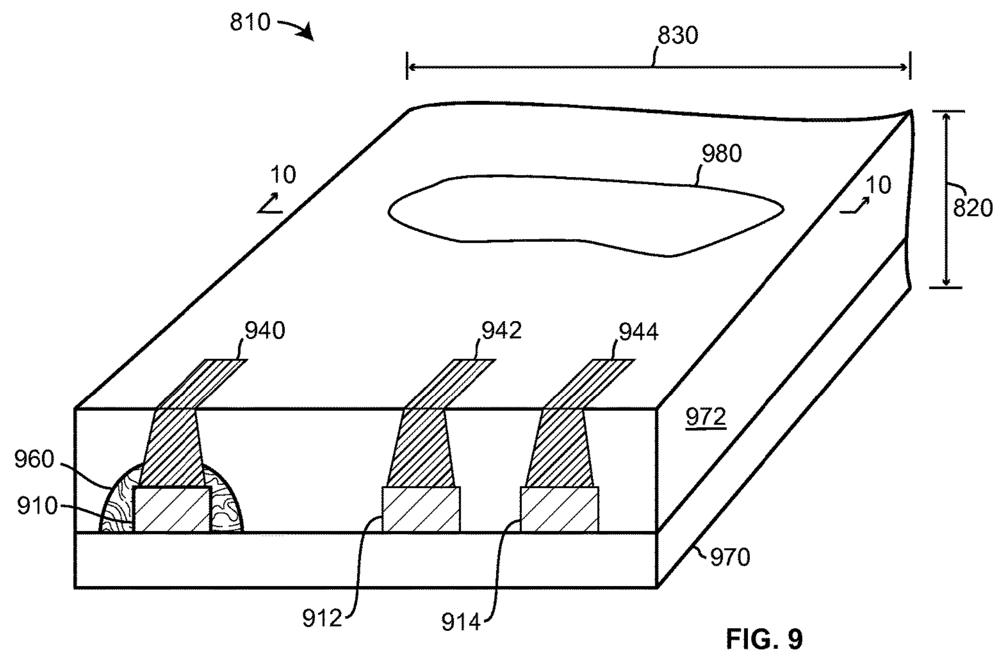
FIG. 9 is a plan view of the moisture sensor of FIG. 8 after deployment.

Pad 810 may be produced with standardized widths and lengths for particular applications. Such widths and lengths may relate to the standard sizes of appliances or kitchen sinks. When extended, pad 810 conforms to the surface upon which it is placed. Pad 810 includes absorbent cover 972 and absorbent substrate 970. Pad 810 may further include a non-absorbent base beneath, with respect to FIG. 9, substrate 970.

Conductors 910-914 are positioned on and coupled to substrate 970. Conductors 910-914 are covered by cover 972. Contacts 940-944 and contacts 1240-1244 mechanically and electrically couple to conductors 910-914 at respective ends of pad 810. Contacts 940-944 are positioned at one end of pad 810 and contacts 1240-1244 at the opposite end of pad 810. Although contacts 940-944 and 1240-1244 are shown spread out along width 830 of pad 810, contacts 940-944 and 1240-1244 may be closely spaced to one edge of pad 810 to permit reader 120 to couple to pad 810 using a mechanical coupler of relatively small size compared to the width of the pad. Reader 120 may couple to contacts 940-944 or 1240-1244 using any type of conventional mechanical and/or electrical connection including clip 600 disclosed above.

Conductor 910 is covered by non-absorbent (e.g., impervious to liquid, waterproof) layer 960 that performs the functions of layer 771 discussed above. Layer 960 prevents or delays establishing a circuit between conductor 910 and 912. In the implementation shown, if substrate 970 is absorbent, liquid may eventually pass under layer 960 to establish an electrical connection between conductor 910 and conductor 912. If the substrate is non-absorbent or less absorbent, a liquid may not be able to establish an electrical connection between conductor 910 and 912 along the length of layer 960.

Figure 10:
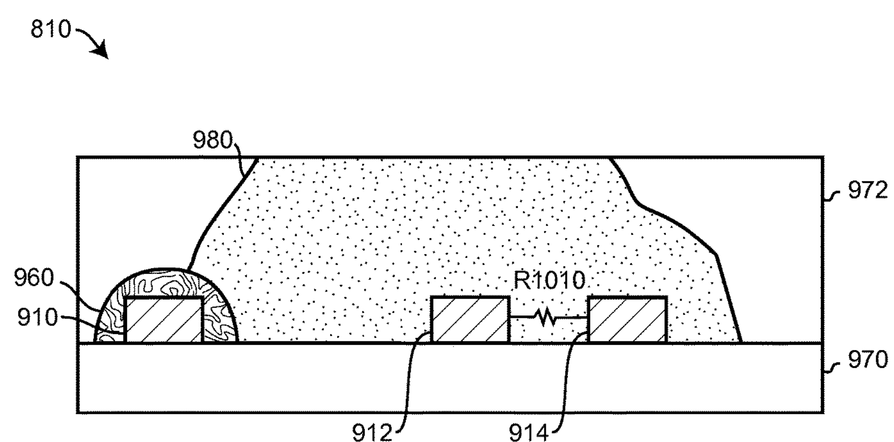
FIG. 10 is a cross-sectional view of the moisture sensor of FIG. 9 at 10-10.
Figure 11:
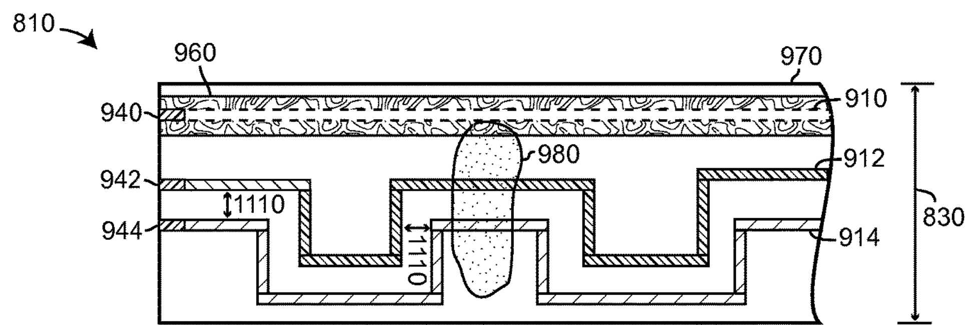
FIG. 11 is a plan view of the conductors of the moisture sensor of FIG. 8.
Figure 12:
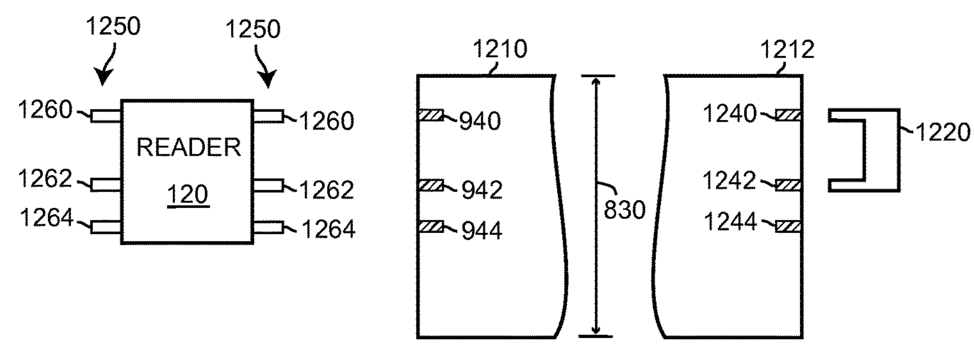
FIG. 12 is a plan view of reader and a cap that couple to the moisture sensor of FIG. 8.

For example referring to FIG. 10, liquid 980 establishes an electrical connection between conductor 912 and 914 via impedance R1010, but not between conductors 910 and 912 or 910 and 914.

Conductors 912 and 914 may have serpentine pattern so that conductors 912 and 914 cover more of the area of pad 810 across width 830. As discussed above, the serpentine pattern may establish zones for detecting and reporting the area of moisture with respect to pad 810. In the implementation of pad 810, space 1110 between conductor 912 and 914 is constant. As discussed above the separation of conductor 912 from 914 need not be constant.

Reader 120 may couple to contacts 940-944 at one end of roll 810, end portion 1210, or contacts 1240-1244 at the other end of roll 810, end portion 1212. Shunt 1220 (e.g., bridge, cap) couples between conductor 910 and 912 at the end not used by reader 120. Shunt 1220 electrically couples conductor 910 to conductor 912. A cap may perform the function of a shunt. Coupling conductor 910 to conductor 912 with shunt 1220 permits reader 120 to detect that it is electrically coupled to conductors 910 and 912 at the other end of pad 810. Shunt 1220 may mechanically and electrically couple to conductors 910 and 912. Shunt 1220 may further mechanically couple to pad 810 to maintain the mechanical and electrical coupling with conductors 910 and 912. Shunt 1220 may mechanically couple to conductors 910 and 912 and pad 810 using any conventional coupling structures. Shunt 1220 may electrically couple to conductors 910 and 912 using any conventional coupling structures.

Conductor 912 has a higher impedance per unit length than the impedance per unit length of any liquid that may penetrate pad 810. The difference in impedance between conductors 910 per unit length and any liquid that may penetrate pad 810 may be at least five times. Conductor 914 has a lower impedance per unit length than the impedance per unit length of any liquid that may be absorbed by pad 810. The difference in impedance between any liquid that may penetrate pad 810 and conductor 914 may be at least five times.

Conductor 910 may have an impedance per unit length that is greater than the impedance of any liquid that may penetrate pad 810 or an impedance per unit length that is less than any liquid that may penetrate pad 810. Conductors 910 and 912 may have the same impedance per unit length. Conductors 910 and 912 may different impedances per unit length. In an implementation where the impedance per unit length of conductor 910 is greater than the impedance of any liquid, conductors 910 and 912 have the same magnitude of impedance per unit length. In an implementation where the impedance per unit length of conductor 910 is less than the impedance of any liquid, conductor 910 has a magnitude of impedance that is at least five times less than the impedance of any liquid that may penetrate pad 810, preferably an order of magnitude less.

When conductors 910 and 912 are electrically coupled together and conductors 910 and 912 have the same magnitude of impedance per unit length, conductors 910 and 912 function in the same manner as conductor 250 or conductor 750 discussed above. When conductors 910 and 912 are electrically coupled together and conductor 912 has an impedance that is greater than any liquid that may penetrate pad 810 and conductor 910 has an impedance that is less than any liquid that may penetrate pad 810, conductor 912 functions in the same manner as conductor 250 or conductors 750 disclosed above. Conductor 914 functions in the same manner as conductor 252 and 752 disclosed above.

In an implementation, reader 120 may include coupler 1250 for coupling to contacts 940-944 or contacts 1240-1244. Coupler 1250 may include any conventional structures for coupling to contacts 940-944 or contacts 1240-1244 and/or pad 810. Coupler 1250 may include protrusions 1260-1264 for electrically coupling to contacts 940-944 respectively or contacts 1240-1244 respectively. Reader 120 may provide a voltage across protrusions 1260 and 1262. Upon applying a voltage, if reader 120 detect a current, reader 120 detects that it is properly coupled to contacts 940 and 942 respectively or contacts 1240 and 1242 respectively, assuming that shunt 1220 has been properly coupled to contacts 940 and 942 or contacts 1240 or 1242 at the opposite end of pad 810. As disclosed above, preferably when coupler 1250 detects that it is properly coupled to contacts 940 and 942 or 1240 and 1242, contact 1264 is also properly coupled to contact 944 or 1244 by default.

When liquid 980 is absorbed by pad 810, liquid 980 establishes an impedance, for example impedance R1010, between conductor 912 and 914. Even though liquid 980 may be absorbed by pad 810 in the vicinity of conductor 910 and between conductors 910 and 912, the likelihood of developing an impedance through the liquid between conductors 910 and 912 is significantly reduced if not entirely eliminated by layer 960 which resists the penetration of liquid 980 to the point of contact with conductor 910.

The methods disclosed above may be used to determine the location of liquid 980 with respect to at least conductor 912. Reader 120 may store information for correlating the position of the liquid with respect to conductors 912 and/or 914 to a position with respect to pad 810.

Because contacts 940-944 are positioned at end portion 1210 of pad 810 and contacts 1240 to 1244 are positioned at the opposite end portion 1212, reader 120 and shunt 1220 may be coupled to the contacts only at the extremities of pad 810, so pad 810 is a fixed length, and as discussed above, may be produced in lengths that are suitable for particular applications.

Figure 13:
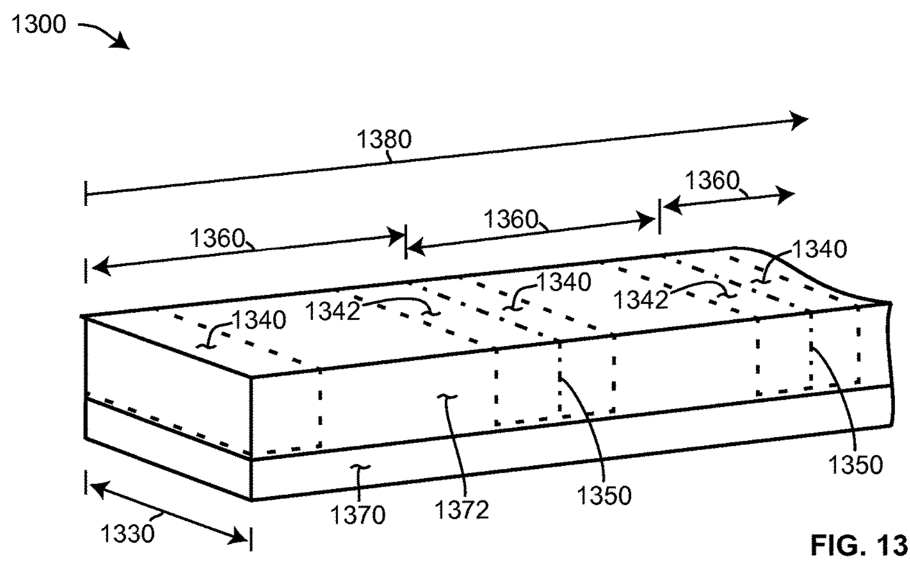
FIG. 13 is a plan view of another implementation of a moisture sensor according to various aspects of the present invention.
Figure 14:
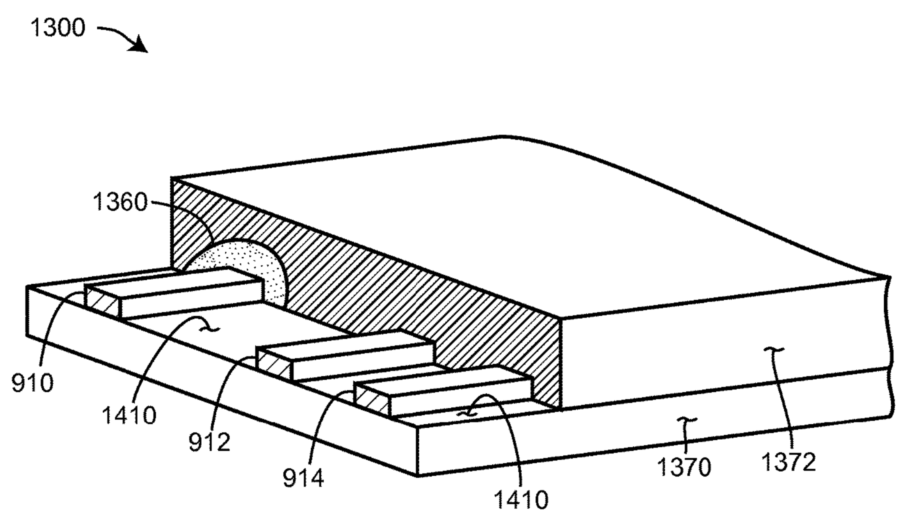
FIG. 14 is a plan view of an exposed area of the conductor of FIG. 13.
Figure 15:
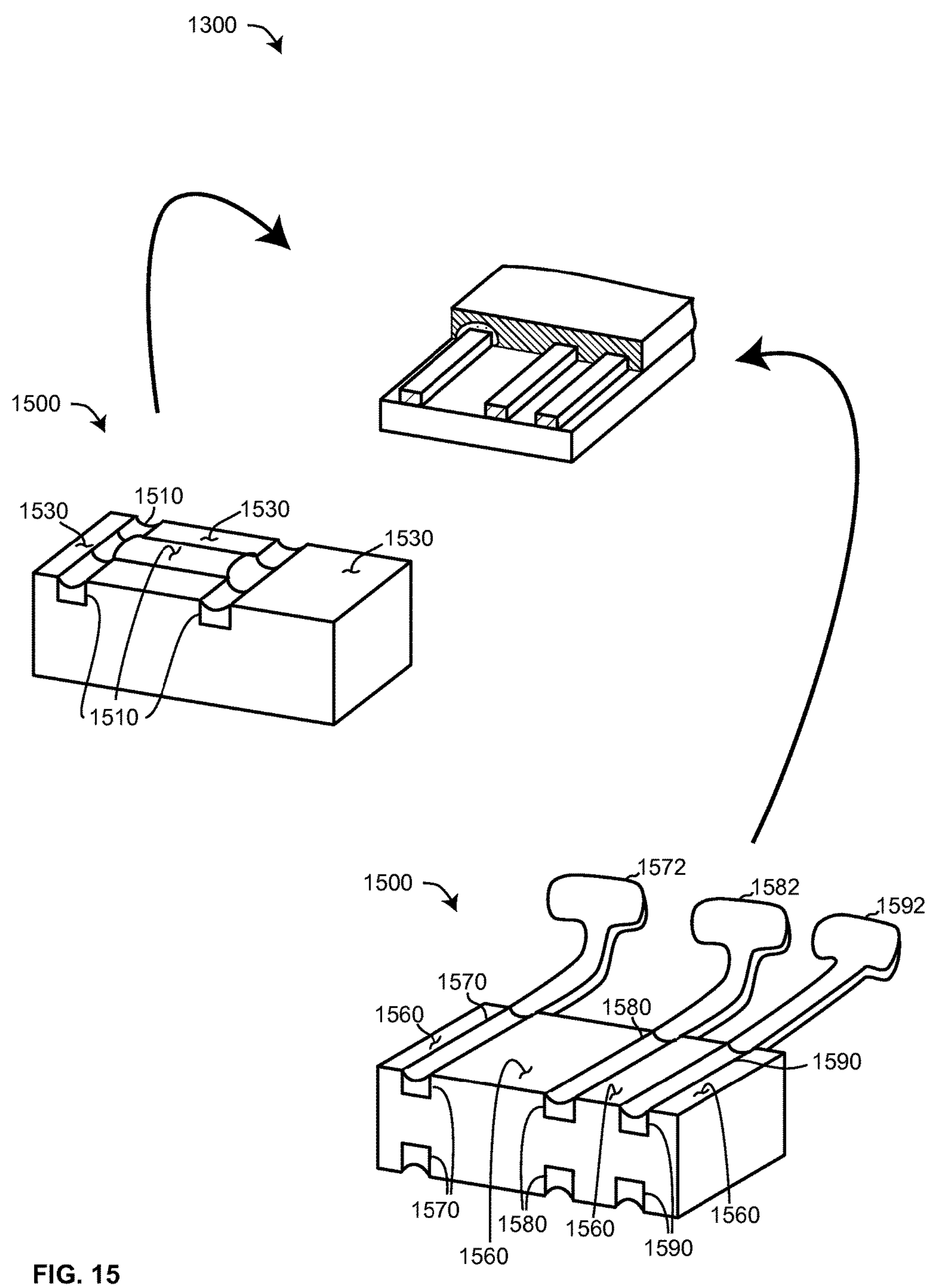
FIG. 15 is a plan view of caps for coupling to the conductors of an exposed portion of the moisture sensor of FIGS. 13 and 14 for coupling a reader.
Figure 16:
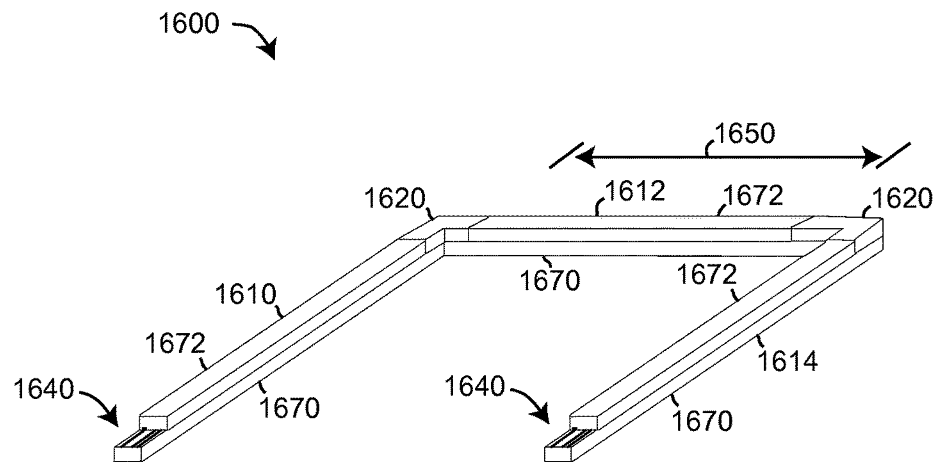
FIG. 16 is a plan view of another implementation of a moisture sensor according to various aspects of the present invention.
Figure 17:
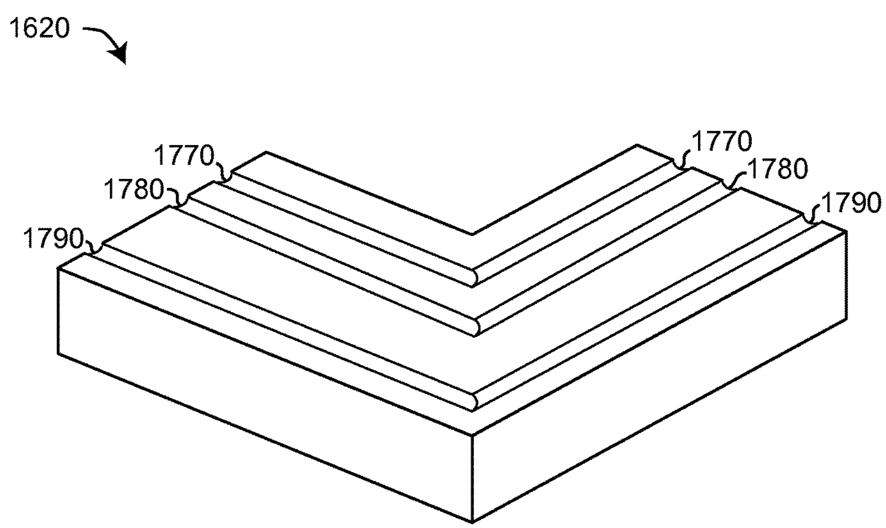
FIG. 17 is a plan view of a corner coupler for the moisture sensor of FIG. 16.

Pad 1300, referring to FIG. 13, is a pad that may be deployed in lengths (e.g., segments) that are less than the total length of pad 1300. Pad 1300 may have width 1330. Pad may have length 1380. Pad 1300 includes substrate 1370 and cover 1372. Pad 1300 performs the functions of pad 810 disclosed above. Substrate 1370 and cover 1372 perform the functions of substrate 970 and cover 972 discussed above.

Length 1380 of pad 1300 may be subdivided into segments 1360. The location of each segment may be indicated on the pad. A line printed on the pad may indicate segment boundaries. Various segments 1360 may be of the same length or different lengths. One or more segments 1360 may be deployed for a use. Segments that are not deployed for a use may be cut away from the segments that will be deployed for a use. A pad may be cut at an indicated segment boundary. Cutting a pad cuts the cover, the conductors, the substrate, and any other layer of the pad.

Tear-away (e.g., removable) portions 1340 and 1342 are positioned at the end portion of each segment 1360 (e.g., proximate to a segment boundary). Removing tear-away portions 1340 and 1342 exposes the conductors of pad 1300 so that a reader and a shunt (e.g., cap) may be coupled to the ends of the segments.

For example, pad 1300 may be cut in any conventional way (e.g., knife, scissors) at any segment termination line (e.g., boundary) 1350. The portion cut from length 1380 of pad 1300 may include one or more segments. Tear-away portions 1340 and 1342 are removed from each end of the portion to expose conductors 910-914. Tear-away portion includes a portion of cover 1372. Tear away portions 1340 and 1342 may be prepared in any conventional way for separation from substrate 1370; however, the integrity of layer 1360 should be left substantially intact so conductor 910 is protected from liquid in the portions of pad 1300 where tear-away sections are not removed. Further, the integrity of cover 1372 over conductors 912 and 914 in the portions of pad 1300 where tear-away sections are not removed should be left substantially intact so that liquid may bridge between conductors 912 and 914 as cover 1372 and/or substrate 1370 absorb liquid.

Removing tear-away portions 1340 and 1342 exposes the conductor 910-914 for coupling a reader and a shunt at respective ends of the pad as discussed above. Read 120 may electrically couple to conductors 910-914 at one end of the portion in any conventional manner while shunt 1220 may couple to conductors 910 and 912 at the other end of the portion.

End caps (e.g., cap) may also be used to perform the functions shunting (e.g., electrical coupling) and mechanical coupling to facilitate coupling a reader to conductors 910-914. An end cap may be referred to as a cap. An end cap may include conductors for electrically coupling to one or more of conductors 910-914. End caps may include conductors or taps for providing access to electrical conductors 910-914 to establish an electrical coupling.

For example, shunt end cap 1500 may be positioned over one exposed end of pad 1300 so that conductor 1510 electrically couples to conductors 910 and 912. Conductor 1510 physically contacts conductors 910 and 912 to establish electrical contact. Surface 1530 of shunt end cap 1500 contacts surface 1410 of pad 1300. Surface 1530 may include an adhesive to retain conductor 1510 of shunt end cap 1500 mechanically and electrically coupled to conductors 910 and 912 of pad 1300. Shunt end cap 1500 may be positioned on either end of pad 1300 by rotating shunt end cap 1500 so that conductor 1510 contacts conductors 910-912 when positioned over the exposed conductors.

Reader end cap 1550 may be positioned over the other exposed end of pad 1300 so that conductors 1570, 1580, and 1590 electrically couples to conductors 910, 912, and 914 respectively. Conductors 1570, 1580, and 1590 physically contacts conductors 910, 912, and 914 respectively to establish electrical contact. Surface 1560 of reader end cap 1550 contacts surface 1410 of pad 1300. Surface 1560 may include an adhesive to retain conductors 1570, 1580, and 1590 of reader end cap 1550 mechanically and electrically coupled to conductors 910, 912, and 914 respectively of pad 1300. Reader end cap 1550 may have conductors 1570, 1580, and 1590 on both sides of reader end cap 1550 so that conductors 1570, 1580, and 1590 may couple to conductors 910, 912, and 914 respectively on either end of pad 1300.

Reader end cap 1550 may include conductive tabs 1573, 1582, and 1592 that electrically couple to conductors 1570, 1580, and 1590 respectively. Reader 120 may electrically and mechanically to tabs 1572, 1582, and 1592 in any conventional manner so that reader 120 electrically couples to conductors 910, 912, and 914. Tabs 1572, 1582, and 1592 may be omitted when conductors 1570, 1580, and 1590 are exposed on both sides of reader end cap 1550 because reader 120 may electrically and mechanically couple to the exposed conductors of reader end cap 1550 to establish an electrical coupling with conductors 910, 912, and 914.

Lengths of pad 1300 may be coupled together using fittings to form a sensor of various shapes and/or sizes. Fittings may couple two lengths of sensor together in line or at an angle. Lengths of sensor and fittings may be used as a modular system to form sensors of a variety of shapes and/or size. A modular system may include shunt and reader end caps used at the ends of the aggregate system as discussed above. A modular system may further include a pad, such as pad 1610, 1612, and 1614 that have a fixed length that may also be coupled together using fittings. Pads 1610-1614 may include cover 1672. Substrate 1670 may be rigid.

For example, modular sensor system 1600 includes sensors 1610-1614 and 90-degree fittings (e.g., couplings) 1620. Sensors 1610-1614 each have a length of length 1650. Any number of sensors may be coupled together using fittings that permit any orientation between the sensors to form a system of any size and/or shape.

The end portions of sensors 1610-1614 are exposed so that conductors 910-914 are accessible for mechanical and electrical coupling. Fittings couple to end portions of sensors 1610-1614 to couple conductors 910, 912, and 914 of one sensor to conductors 910, 912, and 914 respectively of another sensor.

Fittings may be of any angle (e.g., 33, 45, 90, 180 degrees). The conductors of the fittings may include conductors positioned to match (e.g., line-up with) the spacing (e.g., positions) of conductors 910, 912, and 914 of the sensors 1610-1614. A surface of a fitting may include an adhesive for coupling to sensors 1610-1614 for retaining mechanical and electrical coupling of the fitting to sensors 1610-1614.

For example, fitting 1620 is an implementation of a 90 degree fitting. Fitting 1620 is positioned with respect to the exposed end portions of two lengths of sensor (e.g., 1610-1614) so that conductor 1770, 1780, and 1790 of fitting 1620 contacts and electrically couples to conductors 914, 912, and 910 respectively of the exposed ends.

End caps for shunting and for a reader, as discussed above, may be coupled to the end portions of an assembled modular system for coupling a reader and detecting moisture.

Modular system 1600 may be used in an implementation of a sensor for detecting a leak in a roof of a building as disclosed in U.S. provisional patent application No. 62/081, 662 ("'662") entitled Methods and Apparatus for Leak Detection in a Roof, filed Nov. 19, 2014 naming Brian C. Woodbury as the first named inventor. The '662 application is incorporated herein by reference. The information disclosed in the '662 application may be used for any purpose in this application. Further, the disclosure of the '622 may considered in terms of replacing the three wire sensors of the '662 application with the sensors disclosed in pads 810, 1300, and/or 1610.

The foregoing description discusses preferred embodiments of the present invention, which may be changed or modified without departing from the scope of the present invention as defined in the claims. Examples listed in parentheses may be used in the alternative or in any practical combination. As used in the specification and claims, the words 'comprising', 'including', and 'having' introduce an open ended statement of component structures and/or functions. In the specification and claims, the words 'a' and 'an' are used as indefinite articles meaning 'one or more'. When a descriptive phrase includes a series of nouns and/or adjectives, each successive word is intended to modify the entire combination of words preceding it. For example, a black dog house is intended to mean a house for a black dog. While for the sake of clarity of description, several specific embodiments of the invention have been described, the scope of the invention is intended to be measured by the claims as set forth below. In the claims, the term "provided" is used to definitively identify an object that not a claimed element of the invention but an object that performs the function of a workpiece that cooperates with the claimed invention. For example, in the claim "an apparatus for aiming a provided barrel, the apparatus comprising: a housing, the barrel positioned in the housing", the barrel is not a claimed element of the apparatus, but an object that cooperates with the "housing" of the "apparatus" by being positioned in the "housing".

What is claimed is:

1. A system for detecting a presence of a liquid, the system comprising:
- a sensor, the sensor including at least two conductors; and
- a reader, the reader including a processing circuit; wherein:
  - prior to exposure of the sensor to the liquid, the processing circuit:
    - provides a current through a first conductor of the at least two conductors;
    - detects a voltage across the first conductor to determine a magnitude of the impedance of the first conductor;
    - in accordance with the magnitude of the impedance, determines a model of the sensor; and
    - provides a notice regarding the model of the sensor; and
  - after exposure of the sensor to the liquid, the reader detects the presence of the liquid.

2. The system of claim 1 wherein:
- the processing circuit further detects a further electrical characteristic of the sensor; and
- the processing circuit interprets the characteristics in light of the model number.

3. The system of claim 1 wherein:
- the processing circuit comprises a store of information; and
- the processing circuit further determines the model of the sensor in accordance with the store of information.

4. The system of claim 1 wherein the reader determines a location of the liquid with respect to the sensor in accordance with the magnitude of the impedance.

5. The system of claim 1 wherein the model correlates to information regarding a physical layout of the sensor.

6. The system of claim 1 wherein prior to exposure of the sensor to the liquid, the processing circuit further:
- provides a voltage across the first conductor; and
- detects a current through the first conductor to determine the magnitude of the impedance.

7. The system of claim 1 wherein the processing circuit stores the magnitude of the impedance.

8. The system of claim 1 wherein, wherein the processing circuit transmits the notice via a communications circuit.

9. The system of claim 1 wherein the processing circuit:
- includes a look-up table; and
- accesses the look-up table to correlate the magnitude of the impedance to the model of the sensor.

10. The system of claim 9 wherein:
- the reader further comprises a communications circuit; and
- the processing circuit receives the look-up table via the communications circuit.

11. A method for determining a model number of a sensor, the method performed by a processing circuit, the sensor for detecting a presence of a liquid, the method comprising:
- prior to exposing the sensor to the liquid:
  - providing a current through a conductor of the sensor;
  - while providing the current, measuring a voltage across the conductor;
- determining in accordance with the current and the voltage a magnitude of the impedance of the conductor;
- in accordance with the magnitude of the impedance, determining the model number of the sensor.

12. The method of claim 11 wherein determining comprises using a look-up table to correlate the magnitude of the impedance to the model number of the sensor.

13. The method of claim 11 wherein determining comprises:
- accessing a store of information;
- using the store of information to correlate the magnitude of the impedance to the model number of the sensor.

14. The method of claim 11 wherein determining comprises:
- receiving information via a communications circuit;
- using the information to correlate the magnitude of the impedance to the model number of the sensor.

15. The method of claim 11 further comprising transmitting a notice via a communications circuit regarding the model number.

16. A method for determining a model number of a sensor, the method performed by a processing circuit, the sensor for detecting a presence of a liquid, the method comprising:
- prior to exposing the sensor to the liquid:
  - providing a voltage across a conductor of the sensor;
  - while providing the voltage, measuring a current through the conductor;

determining in accordance with the current and the voltage a magnitude of the impedance of the conductor;

in accordance with the magnitude of the impedance, determining the model number of the sensor.

17. The method of claim 16 wherein determining comprises using a look-up table to correlate the magnitude of the impedance to the model number of the sensor.

18. The method of claim 16 wherein determining comprises:

receiving information via a communications circuit;

using the information to correlate the magnitude of the impedance to the model number of the sensor.

19. The method of claim 16 further comprising transmitting a notice via a communications circuit regarding the model number.

* * * * *